United States Patent [19]
Newson

[11] Patent Number: 5,810,814
[45] Date of Patent: Sep. 22, 1998

[54] BONE FIXING SCREW PIN

[76] Inventor: Charles James Newson, 88 Silverdale Avenue, Walton on Thames, Surrey, KT12 1EL, United Kingdom

[21] Appl. No.: 792,486

[22] Filed: Jan. 30, 1997

Related U.S. Application Data

[63] Continuation of Ser. No. 533,187, Sep. 25, 1995, abandoned.

[51] Int. Cl.[6] .................................................. A61B 17/70
[52] U.S. Cl. ............................................. 606/59; 606/54
[58] Field of Search ................................. 606/73, 60, 61, 606/54, 55, 56, 57, 58, 59; 411/398, 400

[56] References Cited

U.S. PATENT DOCUMENTS

| | | | |
|---|---|---|---|
| 131,100 | 9/1872 | Hubbard | 411/400 X |
| 246,151 | 8/1881 | Carrel . | |
| 1,997,466 | 4/1935 | Longfellow | 606/57 X |
| 2,422,841 | 6/1947 | McClain | 411/400 X |
| 2,459,879 | 1/1949 | Hardwick | 411/400 X |
| 3,295,807 | 1/1967 | Von Volkli | 411/400 X |
| 4,475,546 | 10/1984 | Patton | 606/57 X |
| 4,920,959 | 5/1990 | Witzel et al. . | |
| 5,382,248 | 1/1995 | Jacobson et al. | 606/60 |
| 5,417,533 | 5/1995 | Lasner | 411/426 |
| 5,468,241 | 11/1995 | Metz-Stavenhagen et al. | 606/61 |

FOREIGN PATENT DOCUMENTS

| | | |
|---|---|---|
| 0 179 599 | 10/1985 | European Pat. Off. . |
| 21260 | 10/1899 | United Kingdom ... 411/400 |
| 2 024 358 | 8/1978 | United Kingdom . |
| 2 114 891 | 8/1979 | United Kingdom . |
| 2 104 782 | 7/1982 | United Kingdom . |
| WO 88/01488 | 3/1988 | WIPO . |

OTHER PUBLICATIONS

"Manipulation and External Fixation of Metacarpal Fractures," 4524 Journal of Bone and Joint Surgery, vol. 63–A (1981) Oct., No. 8, Boston, Massachusetts, USA.

*Primary Examiner*—Guy V. Tucker
*Attorney, Agent, or Firm*—Iandiorio & Teska

[57] ABSTRACT

A bone fixing screw pin (18) for use in joining broken bones, which screw pin comprises a screw threaded portion (26) for screwing into a bone (22), and a head portion (28), the head portion (28) being such that it bends back on itself and forms an aperture (30) for receiving part of a locking device (20). Connecting members (40) are connected to several of the bone fixing screw pins (18) in order to form bone fixing apparatus (16).

6 Claims, 10 Drawing Sheets

Fig. 1.

PRIOR ART

Fig. 2.

PRIOR ART

BONE FIXING SCREW PIN

This is a continuation of application Ser. No. 08/533,187, filed Sep. 25, 1995, now abandoned.

This invention relates to a bone fixing screw pin for use in joining broken bones.

In order to join broken bones, it is well known to drill the bone either side of a break to be joined, and to insert bone fixing screw pins which form an anchorage for a mechanical support. The mechanical support holds the bone in the correct position until natural healing occurs. The bones may be broken as a result of an accident or they may be broken in order to correct a deformation. The bones may be human bones or they may be animal bones. The combination of the bone fixing screw pins and the mechanical support forms bone fixing apparatus which is often known as an external fixator.

The most commonly used type of bone fixing apparatus comprises four of the screw pins in line, with two of the screw pins being positioned on either side of the bone break, and with both pairs of screw pins being clamped to two short beams. The mating ends of the beams are fixed together by means of a universal coupling. When the break in the bone has been set, the various parts of the bone fixing apparatus are locked rigid in order to enable healing of the break in the bone. This known type of bone fixing apparatus has several disadvantages. More specifically, the holes which need to be drilled in the bone to receive the screw pins have to be drilled by a surgeon accurately in line and this is very difficult, or alternatively, each screw pin has to be accommodated with a ball joint, which makes the bone fixing apparatus costly to produce. Also, the connecting beam between each pair of screw pins also requires ball joints, further increasing the cost and also causing the bone fixing apparatus to be heavy.

It is an aim of the present invention to provide a bone fixing screw which enables bone fixing apparatus to be produced which is light, cheaper and easier to use than existing bone fixing apparatus of the type mentioned above.

Accordingly, the present invention provides bone fixing apparatus for use in joining a broken bone, which bone fixing apparatus comprises at least two screw pins for being screwed to the bone, a connecting member for connecting the two screw pins together, and at least two screw threaded locking devices for locking the connecting member to the screw pins:

the two screw pins each comprising a screw threaded portion for screwing into the bone, and a hook shaped head portion;

the connecting member being a one piece fixed length connecting member which extends in use of the bone fixing apparatus alongside the head portions;

the two locking devices being connected one to each head portion of the two screw pins such that each said locking device extends transversely with respect to the head portion and the connecting member and acts to lock the connecting member to the head portion with the connecting member causing the head portions to be in line with each other;

and the bone fixing apparatus being such that the locking devices are able to be partially tightened in order to connect the connecting member to the head portions of the screw pins whilst allowing the connecting member to move about the head portions whereby multi-directional movement is afforded at each connection point formed by the head portion of one of the screw pins, the connecting member and one of the locking devices prior to full tightening of the locking devices when the bone fixing apparatus is in a required position.

Each said head portion may have two parts which extend parallel to each other.

The locking device is preferably a nut and bolt locking device. Other types of locking device may however be employed. The nut and bolt locking device preferably includes a plain washer. The nut and bolt locking device may also include a splined washer, a spring member, and a clamping collar, the bolt then being a threaded and splined bolt.

The bone fixing apparatus may include the connecting member. The connecting member is preferably a connecting rod but other types of connecting member may be employed.

The connecting member may have one end which is provided with a device for connecting the connecting member to another connecting member.

The device may comprise a first part for connecting to one of the connecting members, a second part for connecting to the other of the connecting members, and means for enabling the device to slide and/or tilt with respect to the first part and/or the second part.

Preferably, the device includes means for increasing or decreasing the distance between the two connecting members which are connected by the device.

The bone fixing apparatus of the present invention may include auxiliary adjustment means for extending between two screw pins positioned adjacent one another on either side of a break in a bone, and for exerting a force on the two screw pins to position the bone at the break. The force exerted on the two screw pins may be a force to keep the bone together at the break or it may alternatively be a force in the opposite direction to lengthen the bone.

Preferably, the auxiliary adjustment means comprises a body, a first screw threaded connector which screws into and out of one end of the body, and a second screw threaded connector with an opposite handed thread which screws into and out of the other end of the body, the first and the second screw threaded connectors being screwable into and out of the body to form the auxiliary adjustment means to a desired length which in use causes the auxiliary adjustment to exert a required force on the two connecting means to position the bone at the break.

The bone fixing apparatus of the present invention can be produced to be lighter, cheaper and easier to use than known bone fixing apparatus. Also, because ball joints are not required, the bone fixing apparatus of the present invention may be stronger in use than the known bone fixing apparatus.

Embodiments of the invention will now be described solely by way of example and with reference to the accompanying drawings in which.

Figure 1:
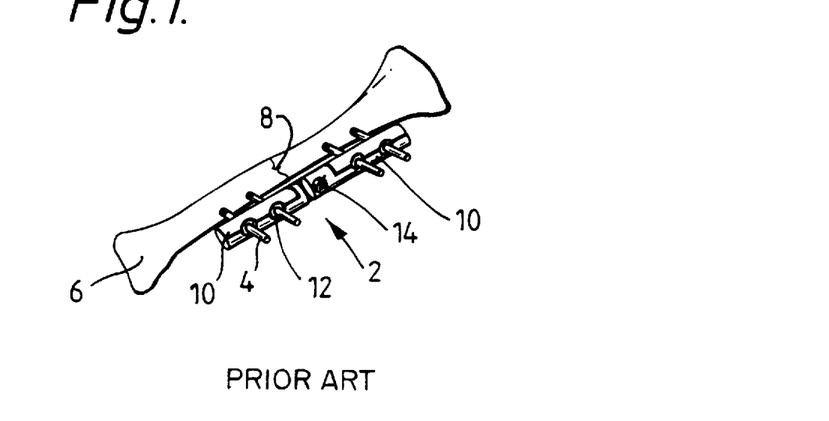
FIG. 1 shows first known bone fixing apparatus in use.

Referring to FIG. 1, there is shown known bone fixing apparatus 2 for connecting together bone fixing screw pins 4 in order to join a broken tibia bone 6. As shown in FIG. 1, the bone 6 has a break 8 and two screw pins 4 are positioned in the bone 6 on either side of the break 8. The screw pins 4 are secured in the bone 6 by a surgeon first drilling four holes in line, and this is difficult to do. The alternative is to provide each screw pin 4 with a ball joint which makes the overall fixing apparatus 2 expensive to produce. As shown in FIG. 1, each pair of screw pins 4 on either side of the break 8 are connected together by a short beam 10. The screw pins 4 pass through the short beams 10 as shown and they are held tightly in position by tightening nuts 12. The two short beams 10 are connected together by a universal joint 14. The entire bone fixing apparatus 2 is expensive to produce, heavy and difficult to fix in position.

Figure 2:
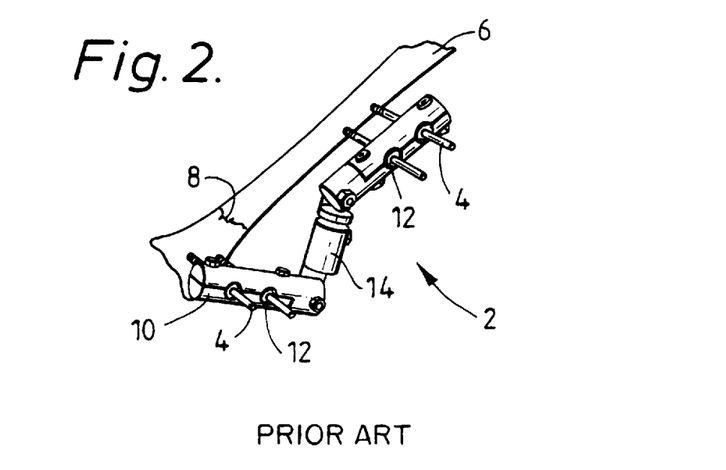
FIG. 2 shows second known bone fixing apparatus in use.

FIG. 2 shows another type of known bone fixing apparatus 2 which is longer than the bone fixing apparatus 2 shown in FIG. 1 and which has been secured in position at the illustrated angle. Similar parts as in FIG. 1 have been given the same reference numerals for each of comparison and understanding. Again it will be appreciated that the bone fixing apparatus 2 shown in FIG. 2 is heavy, expensive to produce and difficult to use.

Figure 3:
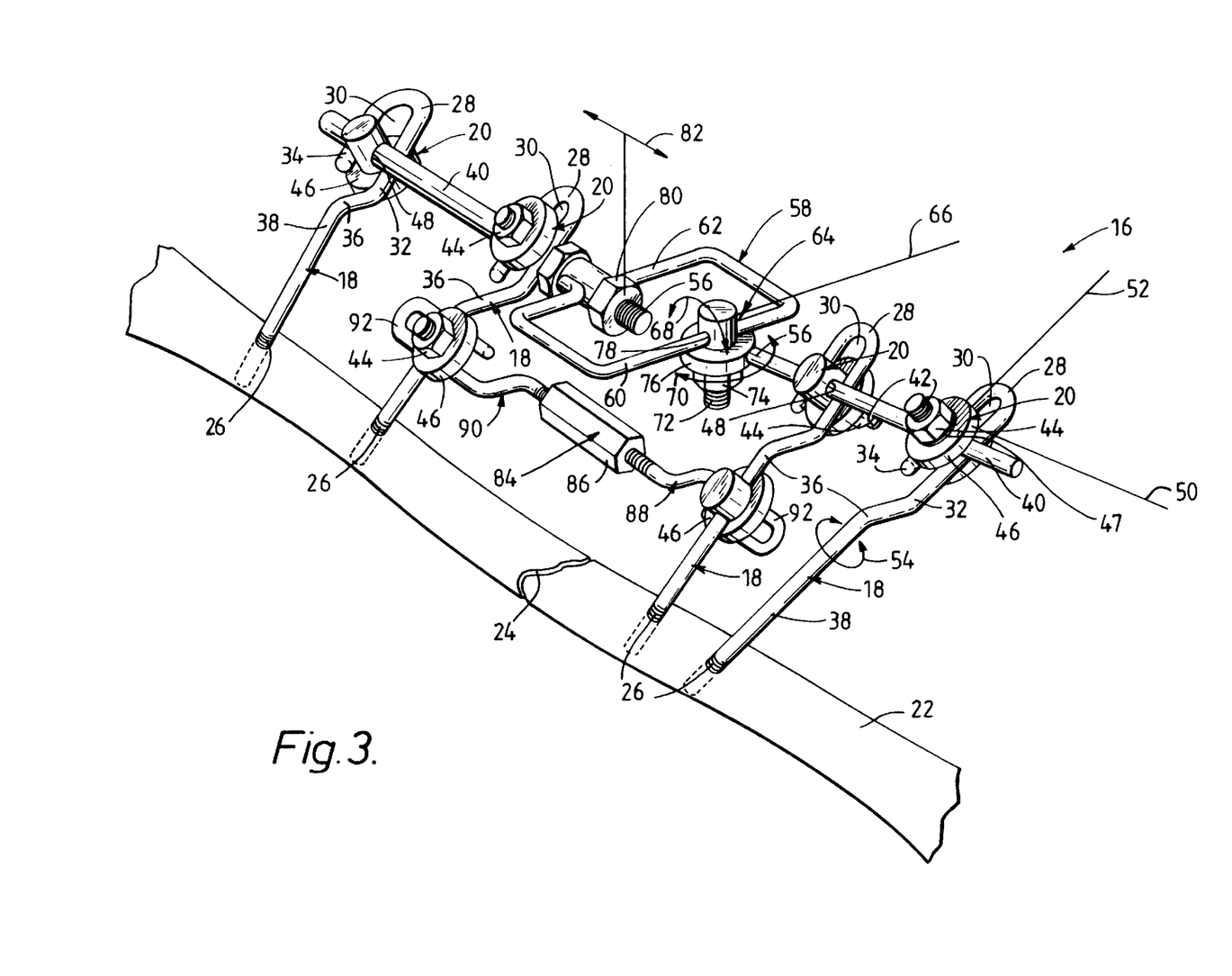
FIG. 3 shows first bone fixing apparatus of the present invention in use.

Referring now to FIG. 3, there is shown bone fixing apparatus 16 comprising four bone fixing screw pins 18 and a locking device 20 for each screw pin 18. As shown, the screw pins 18 are for use in joining a bone 22 having a break 24.

Each screw pin 18 comprises a screw threaded portion 26 for screwing into the bone 22, and a head portion 28. The head portion 28 is such that it bends back on itself and forms an aperture 30 for receiving part of the locking device 20. The head portion 28 bends back on itself such that the aperture 30 is an open ended slot. More specifically, the head portion 28 bends back on itself such as to form two parts 32, 34 which extend parallel to each other and which define sides of the open ended slot.

Each screw pin 18 includes a cranked portion 36 which connects the head portion 24 to a non-threaded shank portion 38. The shank portion 38 is positioned between the crank portion 36 and the screw threaded portion 26. The screw pins 18 are made from a single piece of rod material, the actual material chosen being a metal of the type currently used for making the known screw pins 4, for example stainless steel.

Each locking device 20 is for locking the head portion 28 of its screw pin 18 to a connecting member 40. As shown in FIG. 3, there are two connecting members 40, with each connecting member 40 connecting two of the screw pins together. Each locking device 20 comprises a bolt 42, a nut 44, a washer 46, and a spring washer 47. The purpose of the spring washer 47 is to apply sufficient holding to allow for manipulation before final tightening. The bolt 42 has a through bore 48 so that the connecting member 40 can pass through the bolt 42. Tightening of the nut 44 thus enables the nut and bolt locking device 20 to clamp the head portion 28 to the connecting member 40 at a desired position along the length of the connecting member 40. FIG. 3 illustrates how, prior to tightening of the locking device 20, the connecting member 40 may be slid in the direction 50 or 52. Screwing of the screw pin 18 into a drilled hole in the bone 26 obviously takes place by turning as shown by the arrow 54, this being prior to connecting the screw pin 18 to the connecting member 40.

The connecting member 40 is in the form of a connecting rod. Each connecting member 40 has one end 56 which is provided with a part of a device 58 for connecting the two connecting members 40 together.

The device 58 comprises a first part 60 for connecting to the end 56 of the right hand connecting member 40 as shown in FIG. 3. The device 58 comprises a second part 62 for connecting to the end 56 of the left hand connecting member 40 as shown in FIG. 3. The device 58 further comprises means 64 for enabling the device 58 to slide in the direction 66 or to rock in one or both of the directions 68, 70. The means 64 is a nut and bolt means 64 having a bolt 72, a nut 74, a washer 76 and a through bore 78 in the bolt 72 for receiving the first part 60.

The end 56 of the left hand connecting member 40 as shown in FIG. 3 is screw threaded for receiving a length adjuster nut 80 which permits sliding backwards and forwards as shown by the arrow 82. Thus the threaded end 56 and the nut 80 form means for increasing or decreasing the distance between the two connecting members 40.

The bone fixing apparatus 16 includes auxiliary adjustment means 84 for extending between the two screw pins 18 which are adjacent one another on either side of the break 24 in the bone 22. The auxiliary adjustment means 84 is for exerting a force on the two screw pins 18 to keep the bone 22 together at the break 24 in order that healing can take place.

The auxiliary adjustment means 84 comprises a body 86, a first screw threaded connector 88 which screws into and out of one end of the body 86, and a second left hand screw threaded connector 90 which screws into and out of the other end of the body 86. The body 86 is provided with flat sides as shown to enable it to be rotated clockwise or anti-clockwise to increase or decrease the overall length of the auxiliary adjustment means 84. Thus the auxiliary adjustment means 84 is easily brought to a desired length. This desired length may be for causing the auxiliary adjustment means 84 to exert a required force on the two screw pins 18 and therefore on the two connecting members 40 to keep the bone 22 forced together at the break 24 to promote swift healing. Alternatively, the applied force may be to keep the bone parts slightly apart at the break 24 if it is desired to lengthen the bone 22.

As can be seen from FIG. 3, the first and the second screw threaded connectors 88, 90 each have a head portion 92 which bends back on itself to form a hook for hooking around one of the screw pins 18. The strainer means 84 is used to give extra compression to the break 24, for example a fracture, and also to allow distraction if required. The strainer means 84 also gives extra rigidity to the entire bone fixing apparatus 16, in addition to allowing the remainder of the bone fixing apparatus 16 to be adjusted whilst the strain is taken.

The device 58 is a simple but effective way of forming a universal coupling between the adjacent ends of the connecting members 40. The screw pins 18 form part of the universal coupling. Clamping of the connector members 40 by tightening the nuts 44 allows the screw pins 18 to turn in the bone and this, together with the ability of the connecting members 40 slide in different directions as described above, affords simple and easy self-alignment between any two screw pins 18 on any one connecting member 40. Thus the bone fixing apparatus 16 can be produced to be light and in a cost effective manner. The bone fixing apparatus 16 is easy to use and it provides a rigid construction when tightened.

Figure 4:
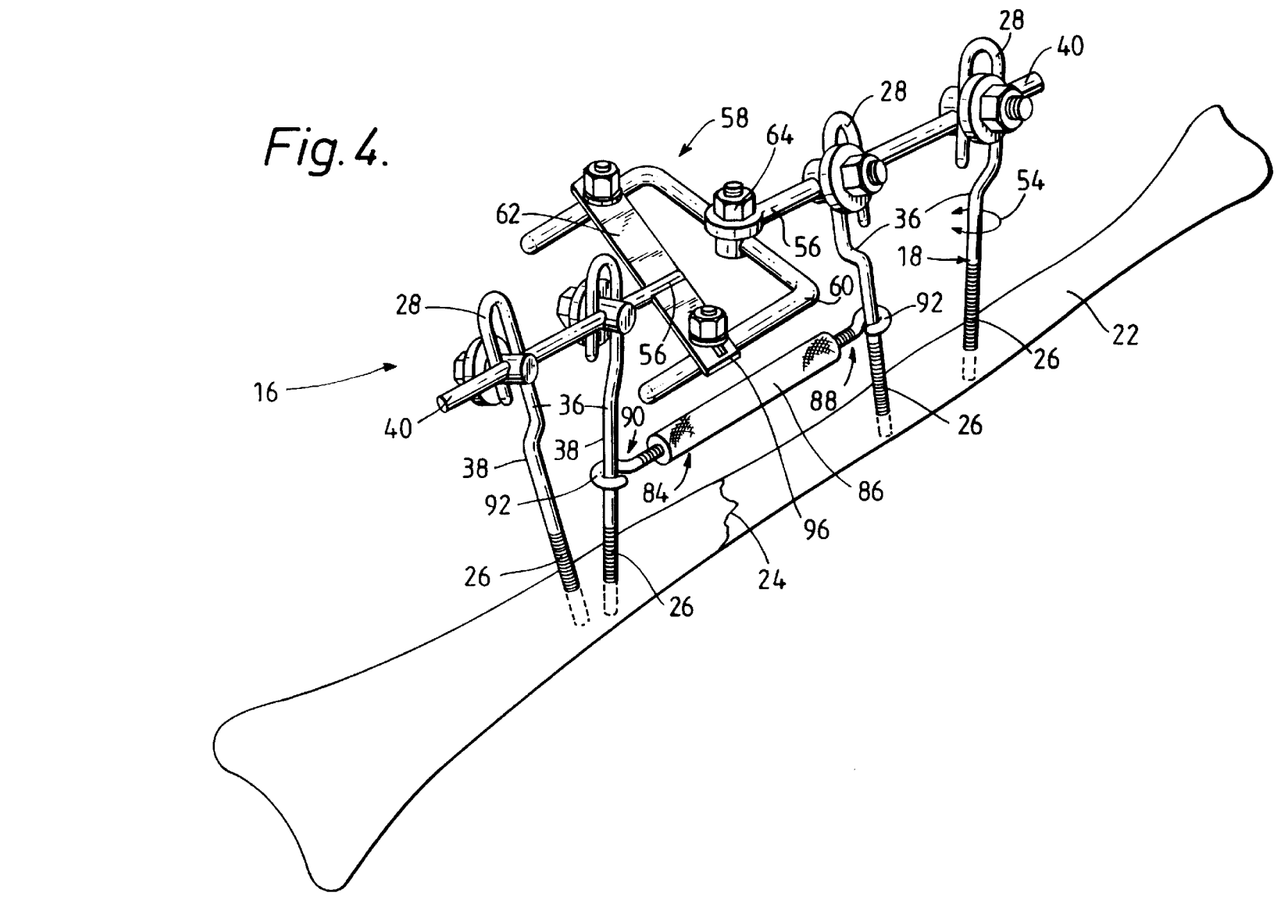
FIG. 4 shows second bone fixing apparatus of the invention in use.

Referring now to FIG. 4, there is shown second bone fixing apparatus 94. Similar parts as in the bone fixing apparatus 16 shown in FIG. 3 have been given the same reference numerals for ease of comparison and understanding.

In FIG. 4, the device 58 is such that the second part 62 forms a yoke which connects to a C-shaped first part 60. The yoke 62 has elongated slots 96 at each end to allow swinging of the yoke 62 until it is locked in position.

In FIG. 4, the body 86 of the strainer means 84 is knurled for rotation rather than being flat sided as shown in FIG. 3.

Figure 5:
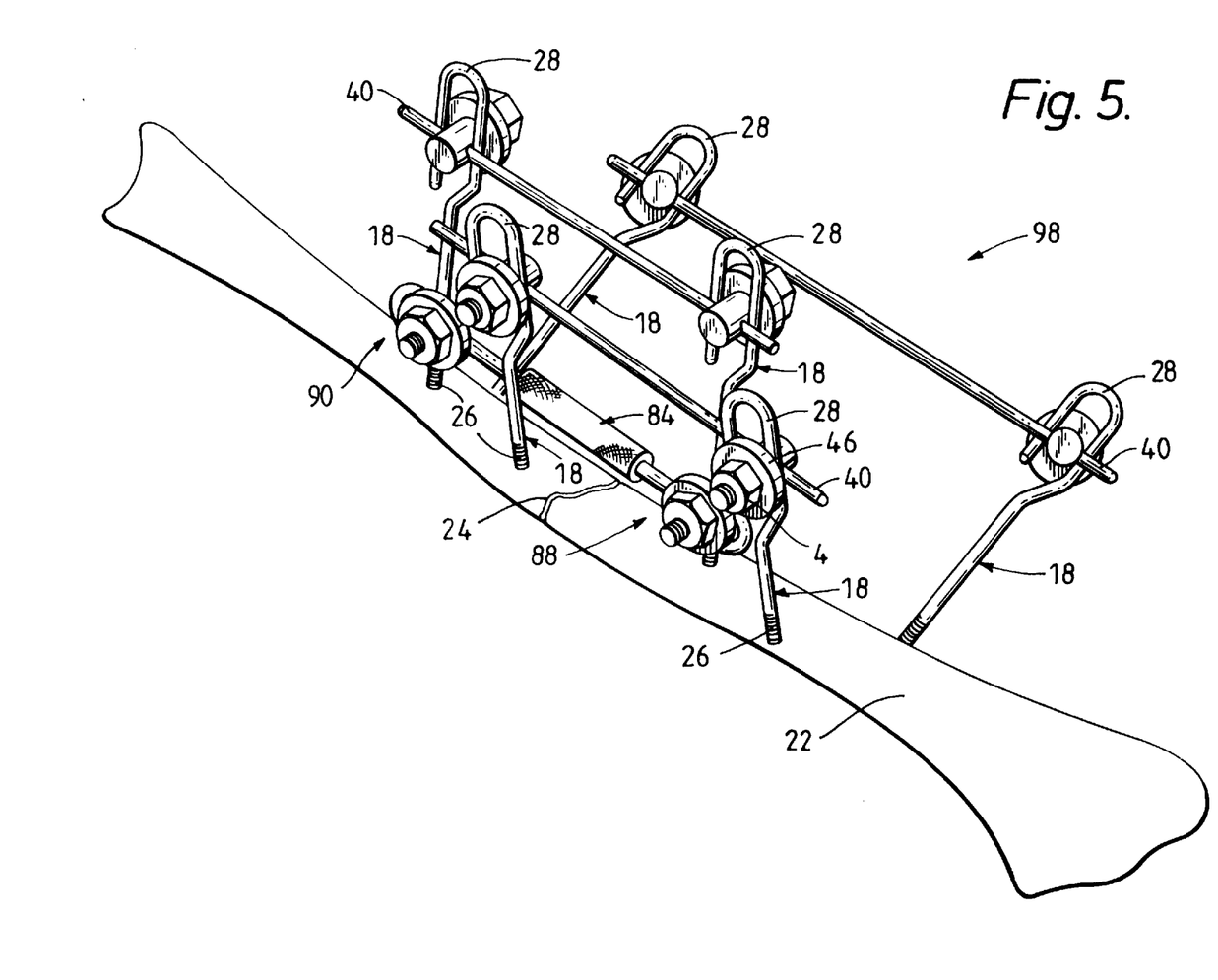
FIG. 5 shows third bone fixing apparatus of the invention in use.

Referring now to FIG. 5, there is shown third bone fixing apparatus 98. Similar parts as in the bone fixing apparatus 16 and 94 shown in FIGS. 3 and 4 respectively have been given the same reference numerals for ease of comparison and understanding.

In FIG. 5, three pairs of screw pins 18 are employed as a way of avoiding using the device 58. The three pairs of screw pins 18 may be cheaper to use than known fixators and they may be thrown away after use. The illustrated outer two pairs of screw pins 18 may be inclined at any suitable and appropriate angle, for example 30°, with respect to the centre pair of screw pins 18. The arrangement shown in FIG. 5 may be used for less complicated fractures of the type that do not require bone manipulation.

Figure 6:
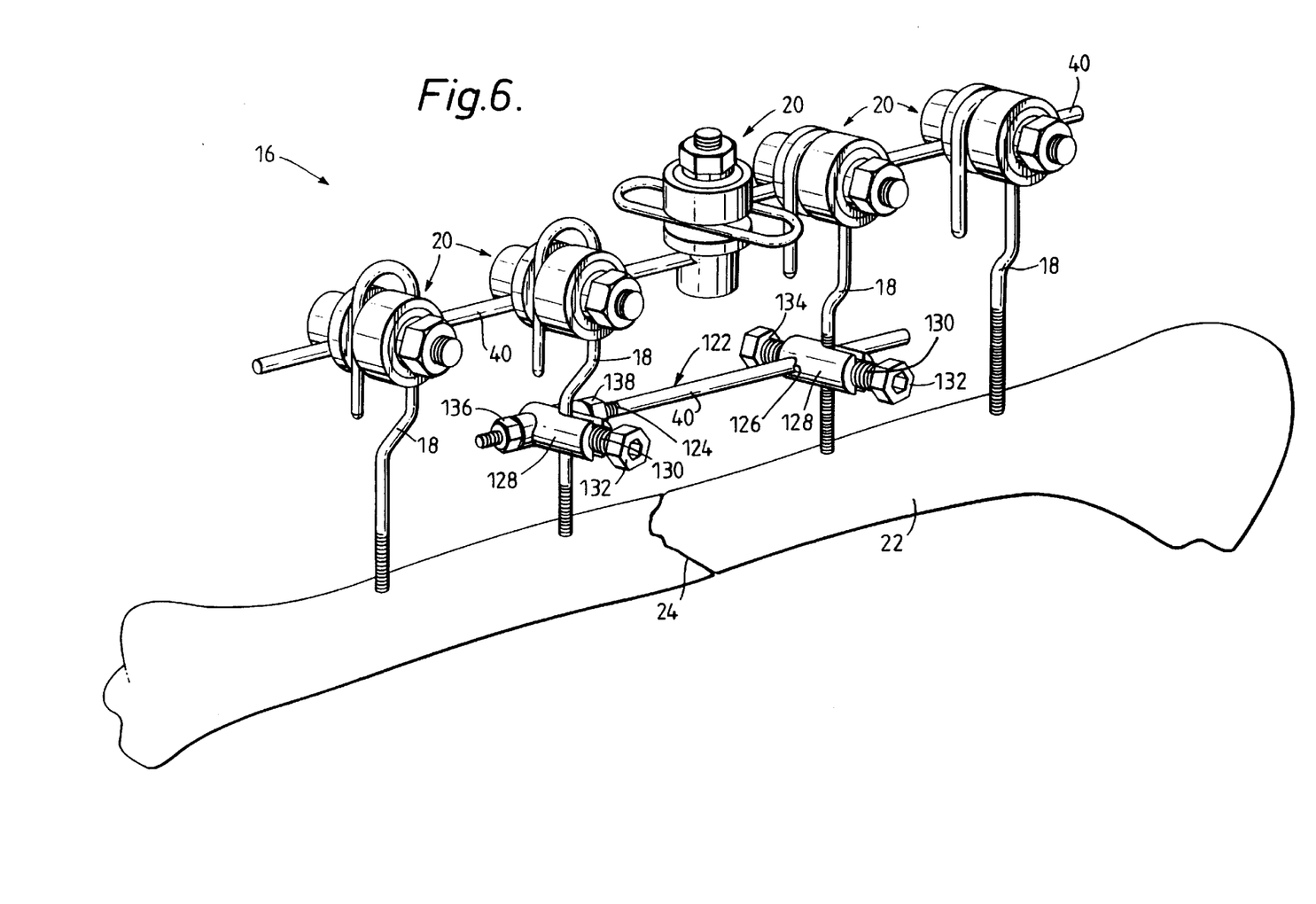
FIG. 6 shows fourth bone fixing apparatus of the invention in use.
Figure 7:
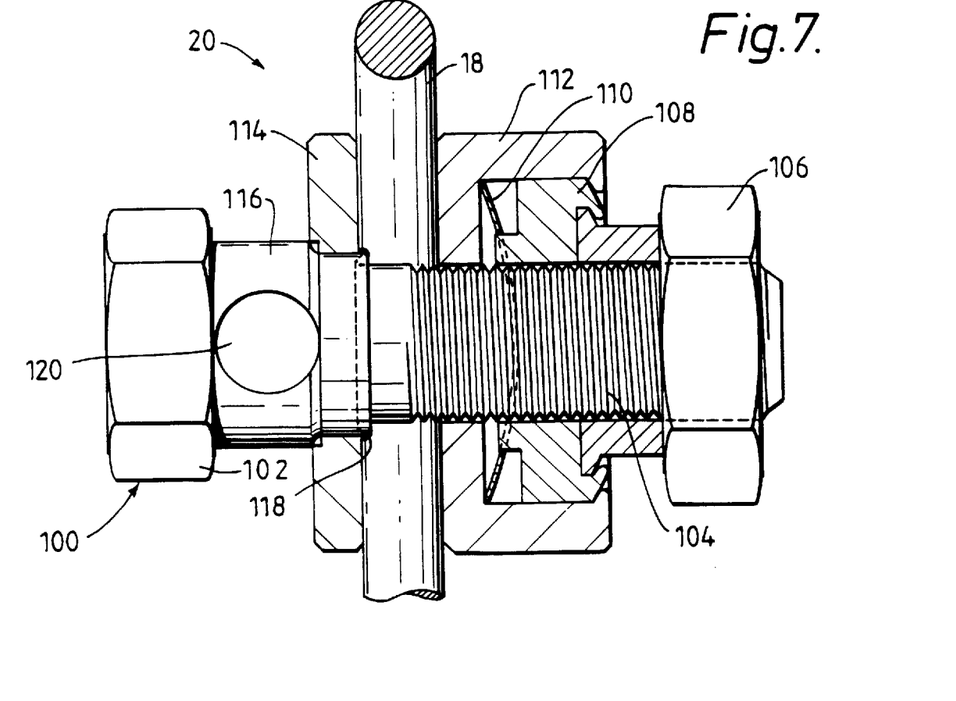
FIGS. 7–16 show parts of a locking device used in the apparatus shown in FIG. 6.
Figure 8:
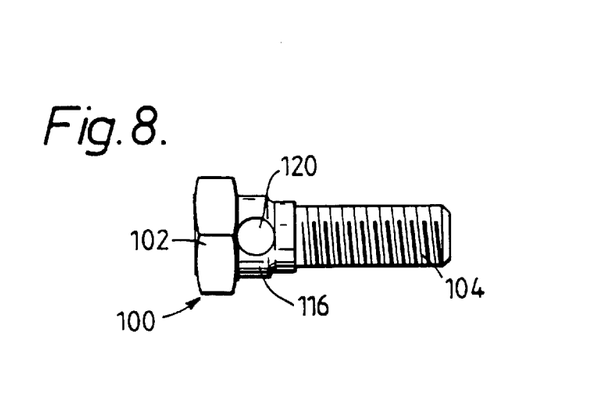
Figure 9:
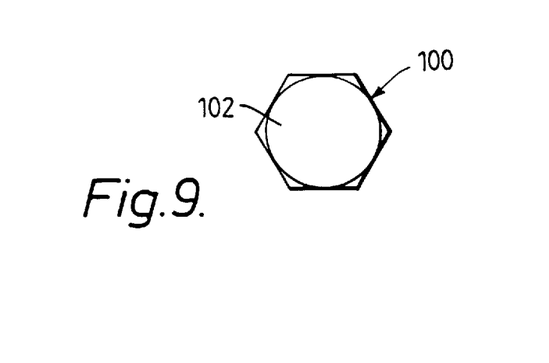
Figures 10, 11, 12, 13, 14, 15, 16:
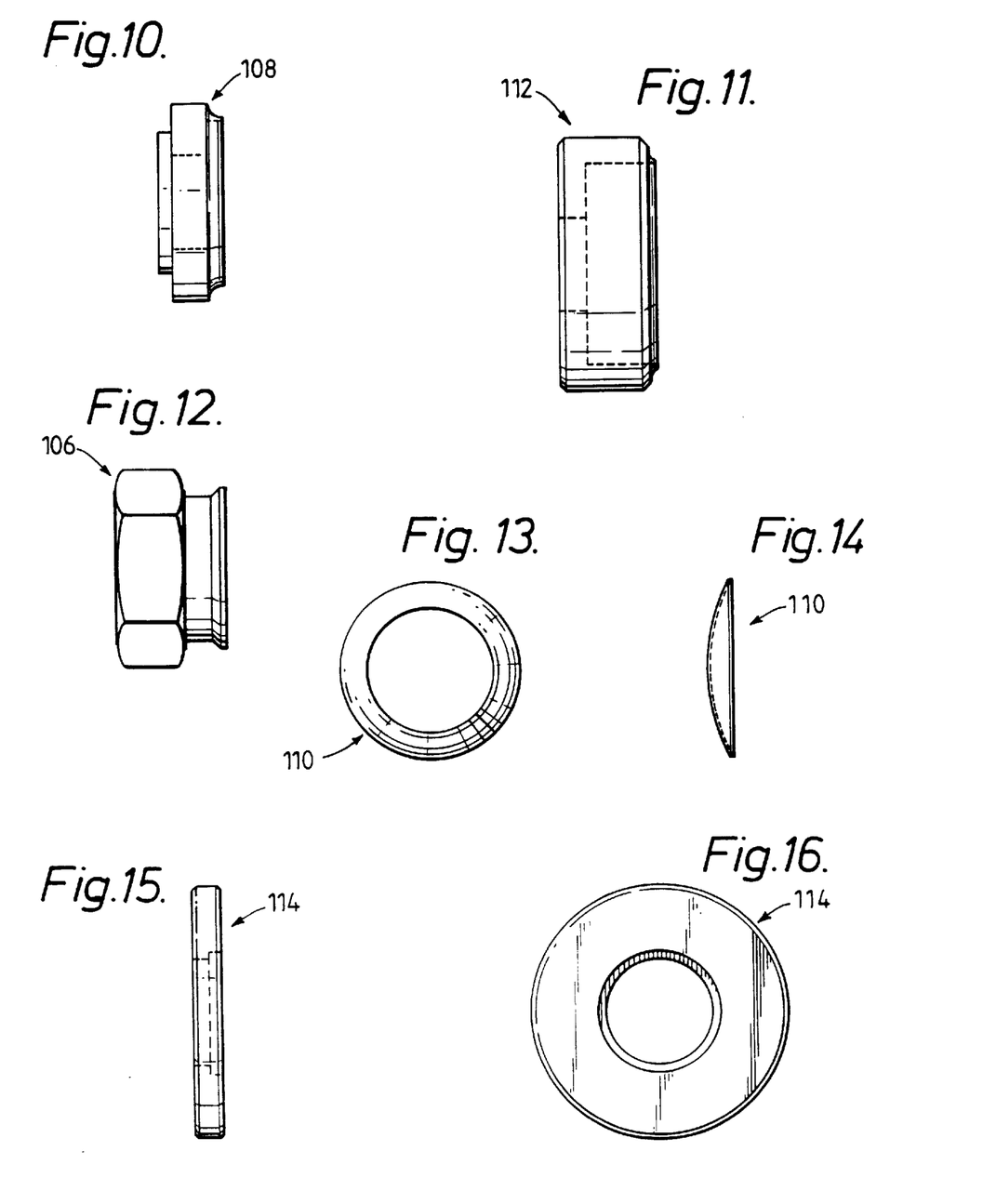

Referring to FIG. 6, there is shown bone fixing apparatus 16 comprising four bone fixing screw pins 18 and a locking device 20 for each screw pin 18. The locking devices 20 are different from the locking devices 20 shown in previous Figures. The construction of one of the locking devices 20 of FIG. 6 is shown in FIGS. 7–13.

The locking device 20 as shown in FIGS. 7–14 is constructed to resist against loosening during use of the bone fixing apparatus 16. The locking device 20 comprises a bolt 100 having a head portion 102 and a shank portion 104. The shank portion 104 is threaded and splined as shown. The shank portion 104 mounts a nut 106, a splined washer 108, a spring member 110 and a clamping collar 112. As shown, the clamping collar 112 abuts against one side of a screw pin 18. A plain washer 114 abuts against the other side of the screw pin 18. The shank portion 104 has an enlarged diameter part 116 which has a pein 118 for use in retaining the washer 114. The shank portion 104 has a hole 120 as shown.

FIG. 6 also shows an arrangement 122 which forms part of the bone fixing apparatus 16 and which is used to give final stability to the remainder of the bone fixing apparatus 16 shown in FIG. 6. Still further, the arrangement 122 is able to enable extra pressure to be applied to the bone 22 at the position of the break 24, thereby to promote faster healing of the break 24. The arrangement 122 comprises a connecting member 40 which is provided with a screw thread 124 at one end. The connecting member 40 is connected to the illustrated two screw pins 18 as shown. More specifically, the right hand end of the connecting member 40 passes through a hole 126 in a tubular member 128. The tubular member 128 is provided with a slot 130 which allows the tubular member 128 to be mounted on the screw pin 18 after the remainder of the bone fixing apparatus 16 has been fixed in position. A screw bolt 132 secures the tubular member 128 to the screw pin 18. A screw bolt 134 locks the connecting member 40 to the tubular member 128.

The left hand end of the connecting member 40 as shown in FIG. 6 is connected to the illustrated screw pin 18 by another one of the tubular members 128 and another one of the bolts 132. The bolt 134 is replaced by an adjusting arrangement comprising locking nuts 136, 138 arranged on either side of the tubular member 128 as shown. By appropriately tightening and loosening the locking nuts 136, 138, tightening pressure can be brought to bear on the break 24 via the connecting member 40 and the two screw pins 18.

Figure 17:
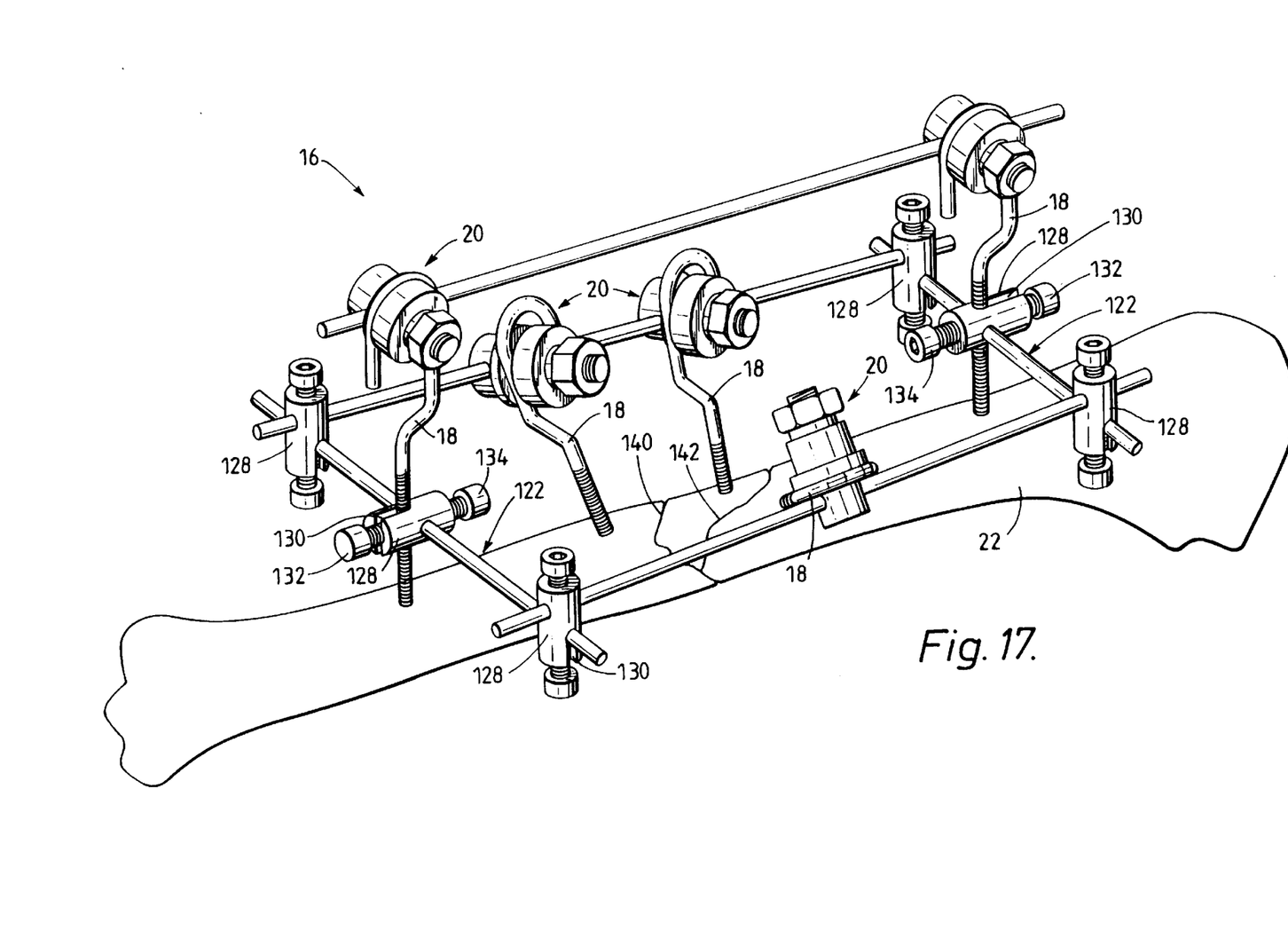
FIG. 17 shows fifth bone fixing apparatus of the invention in use.

FIG. 17 shows fifth bone fixing apparatus 16 which employs a different construction to that shown in FIG. 6 and which is for use when the bone 22 has a more complicated fracture, such as a fracture having two breaks 140, 142. In FIG. 17, it will be seen that five screw pins 18 are required satisfactorily to hold the breaks 140, 142 together. Use of the tubular members 128 with their slots 130 facilitates an easy fitting together of the bone fixing apparatus 16, and especially the fitting together of the illustrated two end arrangements 122 which can be provided after the fixing of the main components of the bone fixing apparatus 16 has taken place.

Figure 18:
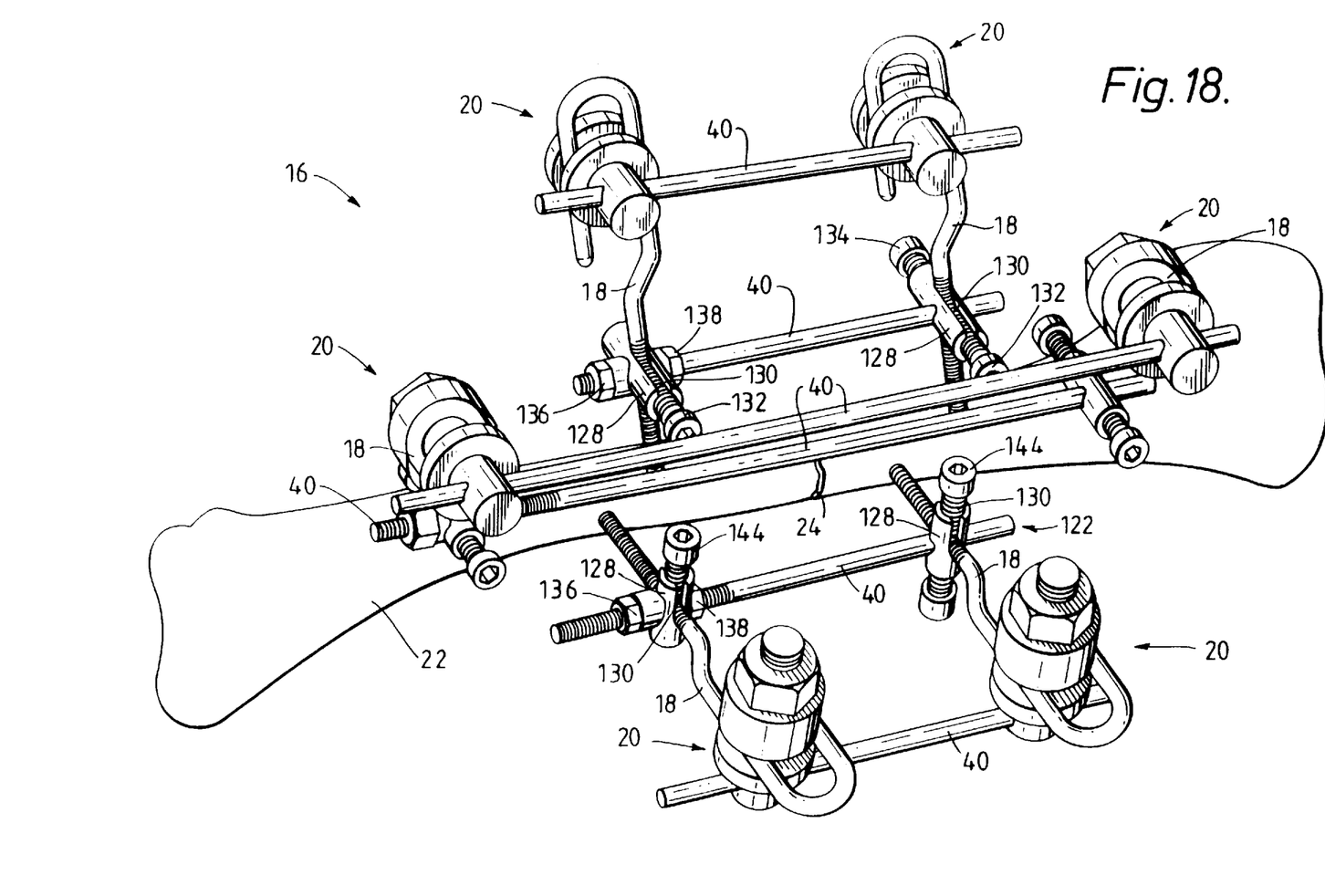
FIG. 18 shows sixth bone fixing apparatus of the invention in use.

FIG. 18 shows sixth bone fixing apparatus 16 secured to a bone 22 having a break 24. The bone fixing apparatus 16 in installed by first of all drilling three pairs of holes in the bone 22, with each pair of holes being substantially in line across the break 24. The screw pins 18 are screwed into position as shown and then the connecting members 40 and the locking devices 20 are installed and connected. A compression arrangement 122 can then be installed using a connecting member 40 and two of the tubular members 128 as shown. The tubular members 128 each have locking screws with recesses 144 for receiving a locking tool.

Figure 19:
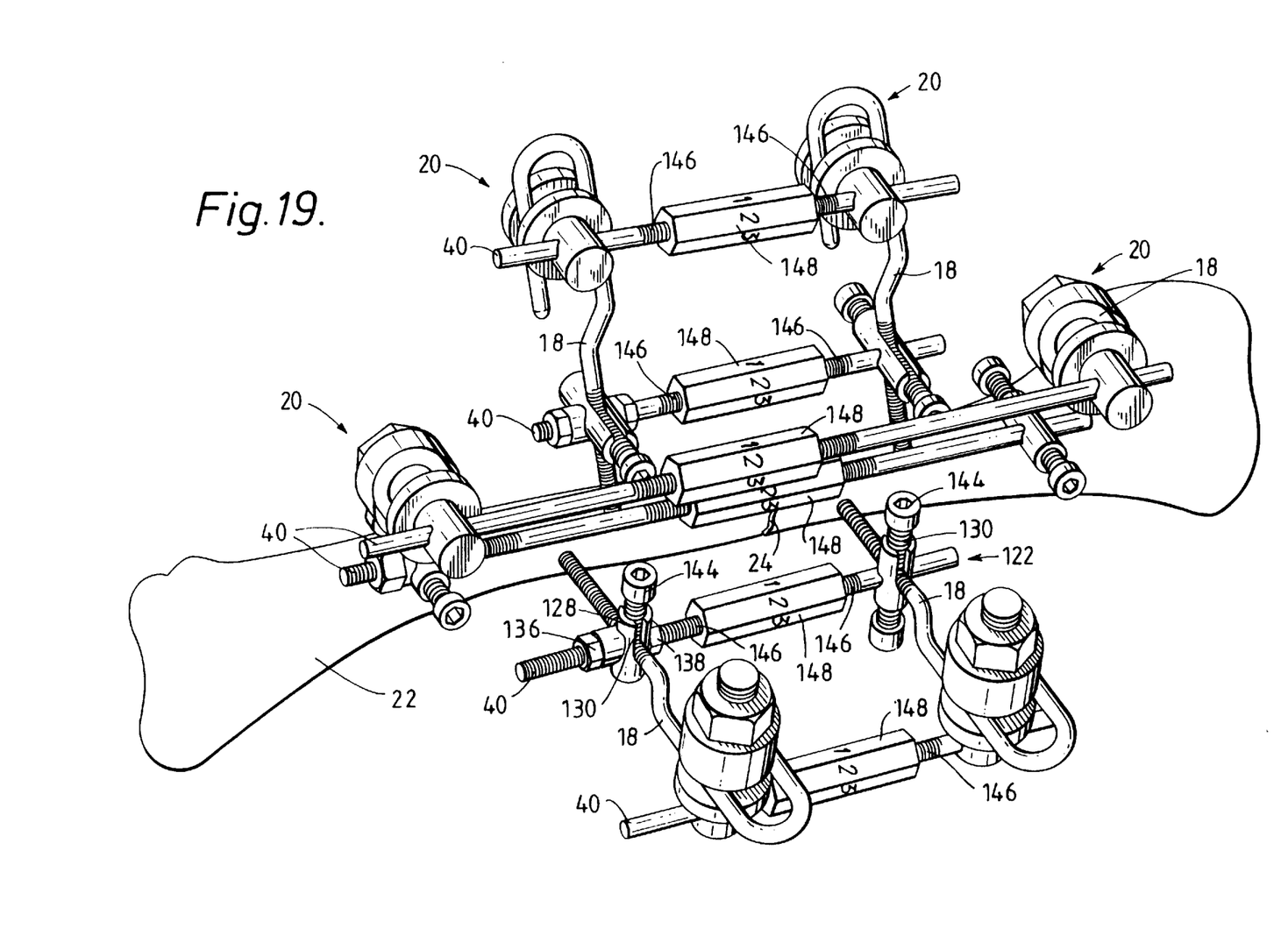
FIG. 19 shows seventh bone fixing apparatus of the invention in use.

FIG. 19 shows seventh bone fixing apparatus 16 which is similar in general layout to the bone fixing apparatus 16 shown in FIG. 18. However, in FIG. 19, it will be seen that each connecting member 40 has effectively been cut in half and provided with a threaded portion 146. The two halves of each connecting member 40 are then connected by the illustrated long nuts 148 which are each marked with the numbers 1,2,3 as shown. The nuts 148 contain opposite handed threads at each end. If it is desired to lengthen the bone 22, the nuts 148 can be periodically turned to the next illustrated progressive number shown on the nuts 148. The turning of the nuts 148 will be at suitable intervals such as to allow the bone 122 to grow and become elongated.

It is to be appreciated that the embodiments of the invention described above with reference to FIGS. 3–19 have been given by way of example only and that modifications may be effected. Thus, for example, the screw pins 18 may have different shaped head portions 28. Also, the devices 58 may be of other constructions.

I claim:

1. Bone fixing apparatus for use in joining a broken bone, which bone fixing apparatus comprises at least two screw pins for being screwed into the bone, a connecting member for connecting the screw pins together, and at least two screw threaded locking devices for locking the connecting member to the two screw pins:

the two screw pins each comprising a screw threaded portion for screwing into the bone, and a hook shaped head portion;

the connecting member being a one piece fixed length connecting member which extends in use of the bone fixing apparatus alongside the head portions;

the two locking devices being connected one to each head portion of the two screw pins such that each said locking device extends transversely with respect to the head portion and the connecting member and acts to lock the connecting member to the head portion with the connecting member causing the head portions to be in line with each other;

and the bone fixing apparatus being such that the locking devices are able to be partially tightened in order to connect the connecting member to the head portions of the screw pins whilst allowing the connecting member to move about the head portions whereby multi-directional movement is afforded at each connection point formed by the head portion of one of the screw pins, the connecting member and one of the locking devices prior to full tightening of the locking devices when the bone fixing apparatus is in a required position.

2. Bone fixing apparatus according to claim 1 in which the connecting member is a rod connecting member, the rod connecting member being such that it is circular in cross section.

3. Bone fixing apparatus according to claim 2 in which each said head portion has two parts which extend parallel to each other.

4. Bone fixing apparatus according to claim 3 in which each said screw pin has a cranked portion which connects the head portion to the remainder of the screw pin, and a shank portion positioned between the cranked portion and the screw threaded portion.

5. Bone fixing apparatus according to claim 1 in which each said locking device includes a washer.

6. Bone fixing apparatus according to claim 1 in which each said locking device is a nut and bolt locking device comprising a nut, a bolt, a splined washer, a spring member, and a clamping collar, the bolt having a body portion which is threaded and splined; and the splined washer, the spring member and the clamping collar fitting on the body portion of the bolt such that the clamping collar is pressed against the connecting member by the spring member and the splined washer when the nut is tightened on the bolt.

* * * * *